(12) United States Patent
Sievert et al.

(10) Patent No.: US 8,552,227 B2
(45) Date of Patent: Oct. 8, 2013

(54) PREPARATION OF HYDROFLUOROOLEFINS BY DEHYDROFLUORINATION

(75) Inventors: Allen Capron Sievert, Elkton, MD (US); Norman A. Carlson, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 576 days.

(21) Appl. No.: 12/634,755

(22) Filed: Dec. 10, 2009

(65) Prior Publication Data
US 2010/0174123 A1    Jul. 8, 2010

Related U.S. Application Data

(60) Provisional application No. 61/142,516, filed on Jan. 5, 2009.

(51) Int. Cl.
*C07C 21/18* (2006.01)

(52) U.S. Cl.
USPC .......................................................... 570/136

(58) Field of Classification Search
USPC .......................................................... 570/136
See application file for complete search history.

(56) References Cited

U.S. PATENT DOCUMENTS

| 4,560,759 A | 12/1985 | Hiratani |
| 5,171,902 A | 12/1992 | Krespan et al. |
| 5,733,981 A * | 3/1998 | Coggio et al. ............. 525/326.2 |
| 6,548,719 B1 * | 4/2003 | Nair et al. ...................... 570/157 |
| 7,897,823 B2 * | 3/2011 | Miller et al. ................... 570/155 |
| 2007/0112230 A1 | 5/2007 | Mukhopadhyay et al. |

FOREIGN PATENT DOCUMENTS

| JP | 7278027 A | 10/1995 |
| JP | 11292807 A | 10/1995 |
| JP | 2004292329 A | 10/2004 |
| WO | WO2008.030439 A2 | 3/2008 |
| WO | WO2008/075017 A2 | 6/2008 |

OTHER PUBLICATIONS

3M THV product series_fluoropolymers_online catalog_(2012).*

* cited by examiner

*Primary Examiner* — Yong Chu

(57) ABSTRACT

A dehydrofluorination process is disclosed for making hydrofluoroolefins of the structure $R_fCH=CHR_f$, wherein each $R_f$ is independently a perfluoroalkyl group or a perfluoroalkyl group having a terminal hydrogen. The process involves reacting $R_fCH_2CHFR_f$ with a basic aqueous solution to produce a product mixture comprising $R_fCH=CHR_f$.

18 Claims, No Drawings

PREPARATION OF HYDROFLUOROOLEFINS BY DEHYDROFLUORINATION

BACKGROUND

1. Field of the Disclosure

This disclosure relates in general to the synthesis of hydrofluoroolefins. More specifically, this disclosure relates to the synthesis of hydrofluoroolefins through dehydrofluorination process.

2. Description of Related Art

CFCs (chlorofluorocarbons) and HCFCs (hydrochlorofluorocarbons) have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. Due to the belief that CFCs and HCFCs are contributing to depletion of stratospheric ozone, there has been extensive work in the past two decades on replacement of these materials with non-ozone depleting substances. Hydrofluorocarbons (HFCs), which do not contain chlorine, have replaced CFCs and HCFCs in a number of applications. Although HFCs do not contribute to the destruction of stratospheric ozone, they are of concern due to their potential contribution to the "greenhouse effect" (global warming). Thus, there is a need for compositions in the applications noted above that do not contribute to the destruction of stratospheric ozone and also have low global warming potentials (GWPs). Certain hydrofluoroolefins, such as 1,1,1,4,4,5,5,5-octafluoro-2-pentene, are believed to meet both goals.

BRIEF SUMMARY OF THE DISCLOSURE

The present disclosure provides a dehydrofluorination process for making hydrofluoroolefins of the structure $R_fCH=CHR_f$, wherein each $R_f$ is independently a perfluoroalkyl group or a perfluoroalkyl group having a terminal hydrogen. The process comprises reacting $R_fCH_2CHFR_f$ with a basic aqueous solution to produce a product mixture comprising $R_fCH=CHR_f$.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

The term "dehydrofluorination", as used herein, means a process during which hydrogen and fluorine on adjacent carbons in a molecule are removed.

The term "alkyl", as used herein, either alone or in compound words such as "perfluoroalkyl", includes cyclic or acyclic and straight-chain or branched alkyl groups, such as, methyl, ethyl, n-propyl, i-propyl, or the different isomers thereof.

The term "a perfluoroalkyl group", as used herein, means an alkyl group wherein all hydrogens on carbon atoms have been substituted by fluorines.

The term "a perfluoroalkyl group having a terminal hydrogen", as used herein, means an alkyl group wherein all hydrogens on carbon atoms, except a single hydrogen on the terminal carbon, have been substituted by fluorines. Examples of a perfluoroalkyl group having a terminal hydrogen include $—(CF_2)_nCF_2H$, wherein n is an integer from 0 to 6.

The term "aralkyl", as used herein, means an alkyl group wherein one or more hydrogens on carbon atoms have been substituted by an aryl group. Examples of an aralkyl group include $C_6H_5CH_2—$.

The term "substituted alkyl group", as used herein, means an alkyl group wherein one or more hydrogens on carbon atoms have been substituted by functional groups, such as hydroxyl groups, halogens, et al., other than aryl groups.

The term "dehydrofluorination product selectivity to $R_fCH=CHR_f$", as used herein, means the molar percentage of $R_fCH=CHR_f$ obtained in the dehydrofluorination reaction of $R_fCH_2CHFR_f$ compared to the total molar amount of all dehydrofluorination products obtained. For example, dehydrofluorination of $CF_3CHFCH_2C_2F_5$ produces $CF_3CH=CHCF_2CF_3$ among other products such as $CF_3CF=CHCHFCF_3$. The dehydrofluorination product selectivity to $CF_3CH=CHCF_2CF_3$ in such a situation is the molar percentage of $CF_3CH=CHCF_2CF_3$ out of the total molar amount of dehydrofluorination products.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Disclosed is a dehydrofluorination process for making hydrofluoroolefins of the structure $R_fCH=CHR_f$, wherein each $R_f$ is independently a perfluoroalkyl group or a perfluoroalkyl group having a terminal hydrogen. The process comprises reacting $R_fCH_2CHFR_f$ with a basic aqueous solution to produce a product mixture comprising $R_fCH=CHR_f$.

In certain embodiments, $R_f$ is independently selected from the group consisting of $—(CF_2)_nCF_2H$, $—(CF_2)_nCF_3$, and $—(CF_2)_nCF(CF_3)_2$, wherein n is an integer from 0 to 6.

Examples of $R_fCH=CHR_f$ in this disclosure include $CF_3CH=CHCF_3$, $CF_3CH=CHCF_2CF_3$, $CF_3CH=CHCF_2CF_2CF_3$, $CF_3CH=CHCF(CF_3)_2$, $CF_3CF_2CH=CHCF_2CF_3$, $CF_3CF_2CH=CHCF_2CF_2CF_3$, $CF_3CH\!=\!CHCHF_2$, $CF_3CH\!=\!CHCF_2CHF_2$, $CHF_2CH\!=\!CHCHF_2$ and $CF_3CF_2CH\!=\!CHCHF_2$.

Hydrofluoroolefins of the structure $R_fCH\!=\!CHR_{f'}$ produced by the dehydrofluorination processes of this disclosure may exist as one of two configurational isomers. For example, $CF_3CH\!=\!CHCF_2CF_3$ and $CF_3CH\!=\!CHCF_3$ may each exist as E- or Z-isomers. As used herein, $R_fCH\!=\!CHR_{f'}$ refers to the isomers, E-$R_fCH\!=\!CHR_{f'}$ or Z-$R_fCH\!=\!CHR_{f'}$, as well as any combination or mixture of such isomers.

In one embodiment of this invention, a process is provided for making 1,1,1,4,4,5,5,5-octafluoro-2-pentene ($CF_3CH\!=\!CHCF_2CF_3$, F12E or HFC-1438mzz) by dehydrofluorination of $CF_3CH_2CHFC_2F_5$ (HFC-449mfe) and/or $CF_3CHFCH_2C_2F_5$ (HFC-449mef). In another embodiment of this invention, a process is provided for making 1,1,1,2,2,5,5,6,6,7,7,7-dodecafluoro-3-heptene ($CF_3CF_2CH\!=\!CHCF_2CF_2CF_3$, F23E or HFC-163-12mczz) by dehydrofluorination of $CF_3CF_2CH_2CHFCF_2C_2F_5$ (HFC-64-13mcfe) and/or $CF_3CF_2CHFCH_2CF_2C_2F_5$ (HFC-64-13mcef). In still another embodiment of this invention, a process is provided for making 1,1,1,4,4,4-hexafluoro-2-butene ($CF_3CH\!=\!CHCF_3$, F11E or HFC-1336mzz) by dehydrofluorination of $CF_3CH_2CHFCF_3$ (HFC-347mef).

Dehydrofluorination of $R_fCH_2CHFR_{f'}$ may generate some dehydrofluorination products other than the desired $R_fCH\!=\!CHR_{f'}$. In some embodiments of this invention, the dehydrofluorination product selectivity to $R_fCH\!=\!CHR_{f'}$ is at least 90 molar percent. In some embodiments of this invention, the dehydrofluorination product selectivity to $R_fCH\!=\!CHR_{f'}$ is at least 95 molar percent.

The $R_fCH_2CHFR_{f'}$ starting materials for the dehydrofluorination process can be made by known methods in the art. For example, HFC-449mfe and HFC-449mef can be made by hydrogenation of perfluoropentene-2 as disclosed in U.S. Pat. No. 5,171,902. HFC-64-13mcfe and HFC-64-13mcef can be made by hydrogenation of $CF_3CF_2CH\!=\!CFCF_2CF_2CF_3$ and $CF_3CF_2CF\!=\!CHCF_2CF_2CF_3$ as disclosed in U.S. Pat. No. 5,171,902. HFC-347mef can be made by hydrogenation of $CF_3CH\!=\!CFCF_3$ as disclosed in Example 4 below.

As used herein, the basic aqueous solution is a liquid (whether a solution, dispersion, emulsion, or suspension and the like) having a pH greater than 7. In some embodiments of this invention, the basic aqueous solution has a pH greater than 10. In some embodiments of this invention, the basic aqueous solution has a pH greater than 12.

In some embodiments of this invention, an inorganic base is used to form the basic aqueous solution. Said inorganic base can be selected from the group consisting of hydroxide, oxide, carbonate, or phosphate salts of alkali, alkaline earth metals and mixtures thereof. In some embodiments, such base can be selected from the group consisting of lithium hydroxide, sodium hydroxide, potassium hydroxide, calcium hydroxide, calcium oxide, sodium carbonate, potassium carbonate, sodium phosphate, potassium phosphate, ammonia and mixtures thereof.

In some embodiments of this invention, the basic aqueous solution is an aqueous solution of a quaternary ammonium hydroxide of the formula $NR_4OH$ wherein each R is independently a $C_1$ to $C_{16}$ alkyl group, aralkyl group, or substituted alkyl group. Examples of $NR_4OH$ compounds useful in this invention are tetra-n-butylammonium hydroxide, tetra-n-propylammonium hydroxide, tetraethylammonium hydroxide, tetramethylammonium hydroxide, benzyltrimethylammonium hydroxide, hexadecyltrimethyammonium hydroxide, and choline hydroxide.

In some embodiments of this invention, the concentration of base in the basic aqueous solution is from about 5 weight percent to about 50 weight percent although the concentration may be limited by the solubility of the base in water. In some embodiments of this invention, the concentration of base in the basic aqueous solution is from about 10 weight percent to about 35 weight percent.

The amount of base (in the basic aqueous solution) typically used to convert $R_fCH_2CHFR_{f'}$ to $R_fCH\!=\!CHR_{f'}$ is from about the stoichiometric quantity (i.e., one mole of base to one mole of $R_fCH_2CHFR_{f'}$) to about five times the stoichiometric quantity. In some embodiments of this invention, it may be desirable (e.g., to increase reaction rate) to employ a ratio of base to $R_fCH_2CHFR_{f'}$ of greater than one. In some embodiments of this invention, the amount of base is from about 1.2 times the stoichiometric quantity to about 3.5 times the stoichiometric quantity. Use of less than the stoichiometric quantity of base will likely result in incomplete conversion of the $R_fCH_2CHFR_{f'}$ starting material which could complicate purification of the $R_fCH\!=\!CHR_{f'}$ product.

Optionally, the $R_fCH_2CHFR_{f'}$ dehydrofluorination process is conducted in the presence of a phase transfer catalyst. As used herein, phase transfer catalyst is intended to mean a substance that facilitates the transfer of ionic compounds into an organic phase from an aqueous phase or from a solid phase. The phase transfer catalyst facilitates the reaction between water-soluble and water-insoluble reaction components. While various phase transfer catalysts may function in different ways, their mechanism of action is not determinative of their utility in the present invention provided that the phase transfer catalyst facilitates the dehydrofluorination reaction.

In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral.

As used herein, cryptands are any of a family of bi- and polycyclic multidentate ligands for a variety of cations formed by joining bridgehead structures with chains that contain properly spaced donor atoms. For example, bicyclic molecules that result from joining nitrogen bridgeheads with chains of (—$OCH_2CH_2$—) groups as in 2.2.2-cryptand (4,7,13,16,21,24-hexaoxa-1,10-diazabicyclo-(8.8.8)hexacosane) is available under the brand names Cryptand™ 222 and Kryptofix™ 222. The donor atoms of the bridges may all be O, N, or S, or the compounds may be mixed donor macrocycles in which the bridge strands contain combinations of different donor atoms.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. In some embodiments of this invention, it is preferred to match crown ether phase transfer catalysts with certain bases used in the basic aqueous solutions. In some embodiments of this invention, crown ether 18-crown-6 is used in combination with potassium hydroxide basic aqueous solution; 15-crown-5 is used in combination with sodium hydroxide basic aqueous solution; 12-crown-4 is used in combination with lithium hydroxide basic aqueous solution. Derivatives of the above crown ethers are also useful, e.g., dibenzo-18-crown-6, dicyclohexano-18-crown-6, dibenzo-24-crown-8 and dibenzo-12-crown-4. Other polyethers particularly useful in combination with basic aqueous solution made from alkali metal compounds, and especially for lithium, are described in U.S. Pat. No. 4,560,759 the disclosure of which is herein incorporated by reference.

In some embodiments of this invention, onium salts include quaternary phosphonium salts and quaternary ammonium salts that may be used as the phase transfer catalyst in the process of the present invention; such compounds can be represented by formulas I and II:

$$R_1R_2R_3R_4P^{(+)}X^{(-)} \quad (I)$$

$$R_1R_2R_3R_4N^{(+)}X^{(-)} \quad (II)$$

wherein each of $R^1$, $R^2$, $R^3$ and $R^4$, which may be the same or different, is an alkyl group, an aryl group, an aralkyl group or a substituted alkyl group, and X is selected from the group consisting of F, Cl, Br, I, OH, $CO_3$, $HCO_3$, $SO_4$, $HSO_4$, $H_2PO_4$, $HPO_4$ and $PO_4$. Specific examples of these compounds include tetra-n-butylammonium hydroxide, tetramethylammonium chloride, tetramethylammonium bromide, benzyltriethylammonium chloride, methyltri-n-octylammonium chloride (also known as Aliquat™ 336), dodecyltrimethylammonium bromide, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. In one embodiment of this invention, benzyltriethylammonium chloride is used under strongly basic conditions. Other useful compounds within this class of compounds include those exhibiting high temperature stabilities (e.g., up to about 200° C.) including 4-dialkylaminopyridinium salts, tetraphenylarsonium chloride, bis[tris(dimethylamino)phosphine]iminium chloride, and tetratris[tris(dimethylamino)phosphinimino]phosphonium chloride. In some embodiments of this invention, the phase transfer catalyst is methyltri-n-octylammonium chloride, tetra-n-butylammonium hydroxide, or their mixture.

In some embodiments of this invention, polyalkylene glycols and their ether derivatives are useful as phase transfer catalysts. In some embodiments of this invention, the polyalkylene glycols and their ether derivatives can be represented by the formula:

$$R^6O(R^5O)_tR^7 \quad (III)$$

wherein $R^5$ is an alkylene group containing two or more carbons, each of $R^6$ and $R^7$, which may be the same or different, is a hydrogen atom, an alkyl group, an aryl group, or an aralkyl group, and t is an integer of at least 2. Such compounds include, for example, glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, and their monoalkyl ethers such as monomethyl, monoethyl, monopropyl and monobutyl ethers of such glycols, and phenyl ethers of such glycols, benzyl ethers of such glycols, and dialkyl ethers such as tetraethylene glycol dimethyl ether and pentaethylene glycol dimethyl ether, and polyalkylene glycol ethers such as polyethylene glycol (average molecular weight about 300) dimethyl ether, polyethylene glycol (average molecular weight about 300) dibutyl ether, and polyethylene glycol (average molecular weight about 400) dimethyl ether.

Mixtures of the above described phase transfer catalysts from within one of the groups may also be useful as well as mixtures of two or more phase transfer catalysts selected from different groups. Examples of these mixtures include crown ethers and onium salts, quaternary phosphonium salts and quaternary ammonium salts, and crown ethers and polyalkylene glycol ethers.

Optionally, the $R_fCH_2CHFR_f$ dehydrofluorination process is conducted in the presence of an organic solvent. In some embodiments of this invention, the organic solvent is selected from the group consisting of benzene and its derivatives, alcohols, alkyl and aryl halides, alkyl and aryl nitriles, alkyl, alkoxy and aryl ethers, amides, ketones, sulfoxides, phosphate esters and mixtures thereof.

In some embodiments of this invention, the organic solvent is selected from the group consisting of toluene, methanol, ethanol, proponal, isopropanol, 2-methyl-2-propanol (tert-butanol), di(ethylene glycol), dichloromethane, chloroform, carbon tetrachloride, acetonitrile, propionitrile, butyronitrile, methyl glutaronitrile, adiponitrile, benzonitrile, ethylene carbonate, propylene carbonate, methyl ethyl ketone, methyl isoamyl ketone, diisobutyl ketone, anisole, 2-methyltetrahydrofuran, tetrahydrofuran, dioxane, diglyme, triglyme, tetraglyme, N,N-dimethyl formamide, N,N-dimethyl acetamide, N-methyl pyrrolidinone, sulfolane, dimethyl sulfoxide, perfluoro-N-methyl morpholine, perfluorotetrahydrofuran, and mixtures thereof. In some embodiments of this invention, the organic solvent is selected from the group consisting of toluene, ethanol, isopropanol, 2-methyl-2-propanol (tert-butanol), di(ethylene glycol), dichloromethane, carbon tetrachloride, acetonitrile, adiponitrile, 2-methyl tetrahydrofuran, tetrahydrofuran, dioxane, diglyme, tetraglyme, and mixtures thereof. In some embodiments of this invention, the organic solvent is tert-butanol, diglyme, or their mixture.

The dehydrofluorination process may be carried out by adding the basic aqueous solution to the $R_fCH_2CHFR_f$ starting material or by adding the $R_fCH_2CHFR_f$ starting material to the basic aqueous solution. Accordingly, in some embodiments of this invention, the basic aqueous solution is added to the $R_fCH_2CHFR_f$ starting material optionally in the presence of an organic solvent and optionally in the presence of a phase transfer catalyst. In other embodiments of this invention, the $R_fCH_2CHFR_f$ starting material, optionally dissolved in an organic solvent, is added to the basic aqueous solution optionally in the presence of a phase transfser catalyst and optionally in the presence of an organic solvent.

The dehydrofluorination process is conducted within a suitable temperature range at which $R_fCH_2CHFR_f$ will dehydrofluorinate. In some embodiments of this invention, the dehydrofluorination process is conducted at a temperature of from about −10° C. to about 100° C. In some embodiments of this invention, the dehydrofluorination process is conducted at a temperature of from about 0° C. to about 70° C.

The reaction pressure is not critical. The reaction can be conducted at atmospheric pressure, super-atmospheric pressure, or under reduced pressure. In some embodiments of this invention, the reaction is carried out at atmospheric pressure.

In some embodiments of this invention, the dehydrofluorination process may be carried out at such a combination of temperature and pressure as to permit the recovery of the $R_fCH=CHR_f$ product by distillation either during or after the reaction. Suitable combinations of temperature and pressure may be readily deduced from the physical properties of the starting material and product by those skilled in the art.

In other embodiments of this invention, the product of the dehydrofluorination may be separated as an insoluble lower layer from the reaction mixture. In still other embodiments of this invention, the product of the dehydrofluorination may be dissolved in the organic solvent and may be recovered by decanting the solvent layer and isolating the product by washing the solvent layer with water or by distilling the solvent/product solution. Further purification may be accomplished by distillation employing techniques well-known in the art. Since the temperatures and pressures of the dehydrofluorination process of this invention are mild, the choice of materials for the reactor, its feed lines, effluent lines, and associated units is based on their stability to basic aqueous solutions.

Typical materials of construction include stainless steels or plastic-lined carbon steel reactors.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Legend

F11E is $CF_3CH=CHCF_3$
F12E is $CF_3CH=CHC_2F_5$
F23E is $CF_3CF_2CH=CHCF_2C_2F_5$
HFC-1327mz is $CF_3CH=CFCF_3$
HFC-347mef is $CF_3CHFCH_2CF_3$
HFC-449mef $CF_3CHFCH_2C_2F_5$
HFC-449mfe is $CF_3CH_2CHFC_2F_5$
HFC-64-13mcef is $CF_3CF_2CHFCH_2CF_2C_2F_5$
HFC-64-13mcfe is $CF_3CF_2CH_2CHFCF_2C_2F_5$ Example 1

Example 1 demonstrates that reaction of a HFC-449mfe/HFC-449mef mixture with KOH in water generates F12E.

A 100 ml three-neck round bottom flask was equipped with a large stirring bar, a thermocouple well, an addition funnel, and a water condenser connected in series to a dry ice trap and nitrogen bubbler. The flask was charged with water (10.7 g), Aliquat® 336 (0.40 g, 1.0 mmole), an HFC-449mef/HFC-449mfe mixture (10.0 g, 42.7 mmoles, molar ratio 0.28:1). The addition funnel was charged with a solution of potassium hydroxide (5.64 g, ca. 85.4 mmoles) dissolved in water (10.7 g). The KOH solution was added to the flask in small portions over the course of about 40 minutes at room temperature. After stirring for an additional hour, GC analysis suggested only partial conversion of the HFC-449's. Additional potassium hydroxide (1.0 g in 1.9 mL of water) was added, and the mixture stirred for an additional two hours. The reaction was treated with 20 ml of water and a small lower layer (5.4 g) was collected. Analysis of the mixture by $^1$H NMR indicated it contained about 67 mole % F12E and 33 mole % HFC-449's.

Example 2

Example 2 demonstrates that reaction of a HFC-449mfe/HFC-449mef mixture with KOH in water/diglyme generates F12E.

A 250 ml three-neck round bottom flask was equipped with a large stirring bar, a thermocouple well, an addition funnel, and a glass stopper (a closed system). The flask was charged with HFC-449mef/HFC-449mfe mixture (53.5 g, 229 mmoles, molar ratio 0.28:1), diglyme (42.6 g, 45.5 mL), and Aliquat® 336 (1.82 g, 4.5 mmoles). The addition funnel was charged with a solution of potassium hydroxide (35.2 g, ca. 533 mmoles) dissolved in water (90.4 g). The flask was cooled to about 10-11° C. and the KOH solution was added dropwise to the flask contents over the course of 2.4 hours with rapid stirring. The resulting dark mixture was stirrred for an additional two hours. The reaction mixture consisted of a dark upper organic layer and a lower orange aqueous layer. The upper layer was separated and treated with 150 mL of cold water to give 42.6 g of product. Analysis by GC-MS indicated it contained a 9:1 ratio of F12E to 449's.

Distillation of the products of several reactions gave a heart cut boiling at 30.6-31.3° C. Analysis by NMR indicated the distillate was 97.8 mole % F12E, 1.1 mole % HFC-449mfe, and 1.1 mole % of $CF_3CF=CHCHFCF_3$.

Example 3

Example 3 demonstrates that reaction of a HFC-449mfe/HFC-449mef mixture with KOH in water/diglyme generates F12E in high selectivity.

A 50 ml three-neck round bottom flask was equipped with a large stirring bar, a thermocouple well, an addition funnel, and a short path distillation head. The flask was charged with a solution of potassium hydroxide (3.21 g, 48 mmoles) dissolved in water (15.0 g), diglyme (9.4 g, 10 mL), and 40% aqueous tetra-n-butylammonium hydroxide (0.78 g, 1.2 mmoles). The addition funnel was charged with HFC-449mef/HFC-449mfe mixture (6.0 g, 25.6 mmoles, molar ratio 0.28:1). The flask was warmed to about 40° C. and the HFC-449 mixture added to the flask over the course of one hour with rapid stirring; during this time the temperature of the reaction was raised to 74.5° C. Analysis of the distillate (2.58 g) by GC-MS indicated it contained F12E (63.4 mass %) and HFC-449's (35.7 mass %); the dehydrofluorination product selectivity to F12E was 98.6%.

Example 4

Example 4 demonstrates the synthesis of HFC-347mef by hydrogenation of HFC-1327mz.

A 210 ml Hastelloy™ C shaker tube was charged with 51.2 g (65 mL) of anhydrous ethanol and 1.5 g of 5% palladium on carbon catalyst. The tube was sealed, cooled in dry ice, and evacuated. HFC-1327mz (20.0 g, 0.11 mole) was condensed into the tube. The tube was then placed in the shaker mechanism, pressurized with hydrogen to 500 psig, and warmed to 90° C. with shaking for about 20 hours. The reaction mixture was transferred to a flask and the product recovered by distillation. The distillate was washed with cold water and phosphate buffer, dried over molecular sieves and re-distilled. The heart cut collected at a head temperature of 29.6-30.6° C. was 95% pure HFC-347mef. The primary impurities were HFC-1327mz (1.8 GC area %) and $CF_3CH_2CH_2CF_3$ (2.6 GC area %).

Example 5

Example 5 demonstrates that reaction of HFC-347mef with KOH in water/tert-butanol generates F11E in high selectivity.

A 50 ml three-neck, round bottom flask was equipped with a stirring bar, a thermocouple well, a glass stopper, and a rubber septum. The flask was charged with 40 weight % aqueous tetra-n-butylammonium hydroxide solution (2.15 g, 3.3 mmoles), tert-butanol (6.99 g), and a solution of 2.665 g (41.3 mmoles) of KOH dissolved in 9.49 g of water. The flask was cooled in an ice-water bath to 4.6° C. and then treated with HFC-347mef (2.8 g, 95% purity, 14.4 mmoles) via syringe. After stirring for seven minutes with ice cooling, a distillation head with a dry ice cooled receiver was connected to the flask. The reaction was allowed to warm to room temperature as stirring was continued for an additional 1.5 hours. The reaction was then warmed to 68.8° C. over the course of 2.75 hours as the product distilled from the reaction flask into the receiver. Analysis of the distillate by $^1$H NMR indicated it contained 94.8 mole % F11E (dehydrofluorination product selectivity to F11E was 100%) with the balance of the distillate being tert-butanol (2.3 mole %) and 1,1,1,3,3,3-hexafluorobutane (2.8 mole %, an impurity in the starting material).

Example 6

Example 6 demonstrates that reaction of a HFC-64-13mcfe/HFC-64-13mcef mixture with KOH in water/tert-butanol generates F23E in high selectivity.

A 100 ml three-neck, round bottom flask was equipped with a stirring bar, a thermocouple well, a glass stopper, and a rubber septum. The flask was charged with 40 weight % aqueous tetra-n-butylammonium hydroxide solution (3.5 g, 5.4 mmoles), tert-butanol (20.0 g), and a solution of 3.22 g (49.9 mmoles) of KOH dissolved in 20.0 g of water. The flask was cooled in an ice-water batch to 5.8° C. and then treated with a HFC-64-13mcfe/HFC-64-13mcef mixture (9.64 g, 95.6% purity, 27.6 mmoles, mcfe/mcef isomer ratio=4:3) via syringe over the course of 11 minutes. The mixture was allowed to warm to room temperature as it stirred for an additional 2.2 hours. The reaction mixture consisted of a dark orange upper organic layer, clear aqueous interlayer, and a clear fluorocarbon lower layer. The lower layer was separated and washed sequentially with 5% aqueous phosphate buffer and water to give 6.62 g of crude product. GC-MS analysis of the crude product indicated the dehydrofluorination product selectivity to F23E was 99.4%. The crude product was dried over molecular sieves and then distilled to 3.15 g of a heart cut boiling at 64-66° C. Analysis by GC-MS indicated it contained 98.5% F23E; the major impurity (1.0%) was 1,1,1,2,2,5,5,6,6,7,7,7-dodecafluoroheptane from the starting material.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A dehydrofluorination process for making hydrofluoroolefins of the structure $R_fCH=CHR_{f'}$ wherein each $R_f$ is independently selected from the group consisting of —$(CF_2)_nCF_2H$, —$(CF_2H)_nCF_3$, and —$(CF_2)_nCF(CF_3)_2$ wherein n is an integer from 0 to 6, comprising reacting $R_fCH_2CHFR_{f'}$ with a basic aqueous solution to produce a product mixture comprising $R_fCH=CHR_{f'}$, wherein the dehydrofluorination product selectivity to $R_fCH=CHR_{f'}$ is at least 90 molar percent.

2. The dehydrofluorination process of claim 1 wherein the pH of said basic aqueous solution is greater than 10.

3. The dehydrofluorination process of claim 1 wherein the pH of said basic aqueous solution is greater than 12.

4. The dehydrofluorination process of claim 1 wherein said basic aqueous solution is made from an inorganic base.

5. The dehydrofluorination process of claim 4 wherein said inorganic base is selected from the group consisting of lithium hydroxide, sodium hydroxide, potassium hydroxide, calcium hydroxide, calcium oxide, sodium carbonate, potassium carbonate, sodium phosphate, potassium phosphate, ammonia and mixtures thereof.

6. The dehydrofluorination process of claim 1 wherein said basic aqueous solution is made from a quaternary ammonium hydroxide of the formula $NR_4OH$ wherein each R is independently a $C_1$ to $C_{16}$ alkyl group, aralkyl group, or substituted alkyl group.

7. The dehydrofluorination process of claim 1 wherein the reaction of said $R_fCH_2CHFR_{f'}$ with said basic aqueous solution is conducted in the presence of a phase transfer catalyst.

8. The dehydrofluorination process of claim 7 wherein said phase transfer catalyst is selected from the group consisting of crown ethers, onium salts, cryptands, polyalkylene glycols, and mixtures and derivatives thereof.

9. The dehydrofluorination process of claim 8 wherein said phase transfer catalyst is a quaternary ammonium salt of formula

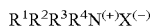

$$R^1R^2R^3R^4N^{(+)}X^{(-)}$$

wherein each of $R^1$, $R^2$, $R^3$ and $R^4$, which may be the same or different, is an alkyl group, an aralkyl group, or a substituted alkyl group, and X is selected from the group consisting of F, Cl, Br, I, OH, $CO_3$, $HCO_3$, $SO_4$, $HSO_4$, $H_2PO_4$, $HPO_4$ and $PO_4$.

10. The dehydrofluorination process of claim 9 wherein said phase transfer catalyst is methyltri-n-octylammonium chloride, tetra-n-butylammonium hydroxide, or their mixture.

11. The dehydrofluorination process of claim 1 wherein the reaction of said $R_fCH_2CHFR_{f'}$ with said basic aqueous solution is conducted in the presence of an organic solvent.

12. The dehydrofluorination process of claim 11 wherein said organic solvent is selected from the group consisting of benzene and its derivatives, alcohols, alkyl and aryl halides, alkyl and aryl nitriles, alkyl, alkoxy and aryl ethers, amides, ketones, sulfoxides, phosphate esters and mixtures thereof.

13. The dehydrofluorination process of claim 12 wherein said organic solvent is tert-butanol, diglyme, or their mixture.

14. The dehydrofluorination process of claim 1 wherein said $R_fCH=CHR_{f'}$ is $CF_3CH=CHCF_2CF_3$ and said $R_fCH_2CHFR_{f'}$ is $CF_3CH_2CHFC_2F_5$ or $CF_3CHFCH_2C_2F_5$ or a mixture of $CF_3CH_2CHFC_2F_5$ and $CF_3CHFCH_2C_2F_5$.

15. The dehydrofluorination process of claim 1 wherein said $R_fCH=CHR_{f'}$ is $CF_3CH=CHCF_3$ and said $R_fCH_2CHFR_{f'}$ is $CF_3CH_2CHFCF_3$.

16. The dehydrofluorination process of claim 1 wherein said $R_fCH=CHR_{f'}$ is $CF_3CF_2CH=CHCF_2CF_2CF_3$ and said $R_fCH_2CHFR_{f'}$ is $CF_3CF_2CH_2CHFCF_2C_2F_5$ or $CF_3CF_2CHFCH_2CF_2C_2F_5$ or a mixture of $CF_3CF_2CH_2CHFCF_2C_2F_5$ and $CF_3CF_2CHFCH_2CF_2C_2F_5$.

17. The dehydrofluorination process of claim 1 wherein the reaction is conducted at a temperature of from about −10° C. to about 100° C.

18. The dehydrofluorination process of claim 1 wherein the dehydrofluorination product selectivity to $R_fCH\!\!=\!\!CHR_f$ is at least 95 molar percent.

\* \* \* \* \*